(12) United States Patent
Klein et al.

(10) Patent No.: US 7,278,315 B1
(45) Date of Patent: Oct. 9, 2007

(54) LASER-ULTRASONIC DETECTION OF SUBSURFACE DEFECTS IN PROCESSED METALS

(75) Inventors: Marvin Klein, Pacific Palisades, CA (US); Todd Sienicki, Los Angeles, CA (US); Jerome Eichenbergeer, Los Angeles, CA (US)

(73) Assignee: Op tech Ventures LLC, Torrance, CA (US)

( * ) Notice: Subject to any disclaimer, the term of this patent is extended or adjusted under 35 U.S.C. 154(b) by 0 days.

(21) Appl. No.: 11/242,969

(22) Filed: Oct. 4, 2005

(51) Int. Cl.
*G01N 29/04* (2006.01)

(52) U.S. Cl. .......................... 73/602; 73/598
(58) Field of Classification Search .......... 73/655–657, 73/625–626, 602; 356/345, 349, 357–360, 356/432, 502–503
See application file for complete search history.

(56) References Cited

U.S. PATENT DOCUMENTS

| | | | | |
|---|---|---|---|---|
| 4,578,584 A | * | 3/1986 | Baumann et al. | 250/341.4 |
| 4,854,710 A | * | 8/1989 | Opsal et al. | 356/432 |
| 5,585,921 A | * | 12/1996 | Pepper et al. | 356/487 |
| 5,760,904 A | * | 6/1998 | Lorraine et al. | 356/513 |
| 5,956,143 A | * | 9/1999 | Kotidis | 356/502 |
| 6,122,060 A | * | 9/2000 | Drake, Jr. | 356/502 |
| 6,128,081 A | * | 10/2000 | White et al. | 356/503 |
| 6,128,092 A | * | 10/2000 | Levesque et al. | 356/451 |
| 6,182,512 B1 | * | 2/2001 | Lorraine | 73/655 |
| 6,628,404 B1 | * | 9/2003 | Kelley et al. | 356/502 |
| 6,747,268 B1 | * | 6/2004 | Ume | 250/227.11 |
| 6,769,307 B1 | * | 8/2004 | Dixon et al. | 73/602 |
| 6,809,991 B1 | * | 10/2004 | Pepper et al. | 367/149 |
| 6,833,554 B2 | * | 12/2004 | Wooh | 250/559.45 |
| 7,082,833 B2 | * | 8/2006 | Heyman et al. | 73/598 |

* cited by examiner

*Primary Examiner*—Helen Kwok
(74) *Attorney, Agent, or Firm*—D. Morgan Tench

(57) ABSTRACT

Subsurface defects in a processed metal are detected by a laser-ultrasonic method involving generation of a surface acoustic wave at one location on the processed metal surface, and detection of a scattered acoustic wave at another location on the processed metal surface. The method can be used in-line to provide real time monitoring of laser cladding and other metal processing operations.

15 Claims, 6 Drawing Sheets

LASER-ULTRASONIC DETECTION OF SUBSURFACE DEFECTS IN PROCESSED METALS

U.S. GOVERNMENT RIGHTS

This invention was made with Government support under a contract awarded by the United States Army. The Government has certain rights in this invention.

BACKGROUND OF THE INVENTION

1. Field of the Invention

The present invention is generally related to processing of metals and alloys, and is more specifically concerned with detection of defects generated near the surface of a workpiece during processing.

2. Description of the Related Art

Advanced metal processing methods are continuously being developed to enable economical manufacture and repair of parts with improved physical properties and often complicated shapes. For example, laser cladding (also called laser powder deposition) is being developed for build-up of stainless steel, titanium and other metals (from metallic powders) to enable near net shape manufacturing and repair of critical parts. Advanced joining methods include laser welding and friction stir welding. The friction stir approach, which involves passing a rotating tool through a solid metallic material, may also be used for friction stir processing (FSP) to locally create a fine-grain microstructure providing improved mechanical properties [F. D. Nicholas, Advanced Materials Processes 6/99, 69 (1999)].

Advanced metal processing typically occurs at high speeds and often involves expensive workpieces and materials so that rapid feedback on the quality of the processed region is critical to controlling scrap rates and costs. Defects that may occur within processed regions of metals include voids, pores, bondlines (incompletely formed bonds), disbonds and cracks. Ideally, such defects would be detected in-line during metal processing so as to minimize scrap and improve product quality via timely corrective action, which could include adjusting processing parameters and/or interrupting the process. Metal processing defects often occur below the surface of the processed region where they cannot be detected by optical, spectroscopic or laser profilometer techniques. Conventional ultrasonic detection methods are sensitive to such subsurface defects but require that the inspected workpiece be in contact with a fluid, which is not practical for in-line use. Inspection methods requiring physical contact between the workpiece and a probe are generally impractical for in-line defect detection. In addition, surface irregularity and roughness typical of processed metal surfaces tend to produce noise signals that interfere with ultrasonic detection based on piezoelectric or EMAT transducers, as well as other conventional methods.

Subsurface defect detection is also a critical requirement for the inspection of cast and forged metals, including ingots and railway rails, for example. Typical defects in ingots and castings include pores and inclusions. Typical defects in railway rails include cracks, which need to be detected in-service.

Laser ultrasonic methods have been developed for non-contact detection of defects in solid parts. Since the "bottom" surface of a part is often inaccessible during machining or processing operations, the most useful laser ultrasonic methods involve both generation and detection on the "top" surface of the part. In this case, a pulsed generation laser beam incident on the part surface at a predetermined generation spot generates ultrasonic waves that propagate within and along the surface of the part. The propagated ultrasonic waves, including those reflected from defects and the bottom surface of the part, are detected via a detection laser beam incident on the part surface at a predetermined detection spot. The propagated ultrasonic waves produce a temporal displacement of the part surface at the detection spot, which is measured via an interferometer that analyzes a portion of the detection laser beam reflected from the part surface. Ultrasonic waves reflected from defects may be distinguished from other reflected ultrasonic waves from the difference in time of arrival of the waves at the detection spot.

Laser ultrasonic methods involving generation and detection on the same surface have been applied to detection of various defects, including voids and cracks, in parts of varied shapes and comprising various materials. These methods have typically involved generation and detection of bulk ultrasonic waves, namely compressional waves, which tend to travel along the surface normal, and shear waves, which tend to travel at angles to the surface normal. Laser ablation produces strong compressional and shear waves, whereas compressional waves produced thermoelastically are relatively weak. Bulk ultrasonic waves are well-suited for detecting defects that are relatively distant from the generation-detection surface. However, bulk ultrasonic waves are not well-suited for detecting near-surface (i.e., subsurface) defects for which the delay time for waves reflected from defects is very short, making ultrasonic measurements difficult.

In addition, application of prior art laser ultrasonic methods has generally been limited to smooth and relatively even surfaces to avoid speckle noise associated with surface roughness and unevenness. In contrast, metallic surfaces processed by laser cladding, friction stirring or other methods tend to be uneven and relatively rough. Consequently, prior art laser ultrasonic inspection methods cannot be directly applied to detection of defects in processed metallic workpieces.

The limitations of prior art laser ultrasonic methods are particularly acute for defect detection during laser cladding. The cladding is typically applied in thin layers and each new layer needs to be inspected for defects before it is buried under subsequently applied layers. This requires detection of subsurface defects that are very near the top surface, which cannot be accomplished using the bulk ultrasonic waves generally employed in the prior art.

The present invention utilizes Rayleigh waves (surface acoustic waves) to detect subsurface defects in processed metallic surfaces. Rayleigh waves have been used in the prior art for characterization of near-surface material properties and for detection of surface-breaking cracks. U.S. Pat. No. 5,894,092 to Lindgren et al. describes use of transducers to generate and detect Rayleigh waves in order to determine near-surface material properties by measuring the Rayleigh wave velocity as a function of frequency. U.S. Pat. No. 4,274,288 to Tittmann et al. describes use of transducers to generate and detect Rayleigh waves in order to determine the depth of a surface-breaking crack through analysis of the ultrasonic frequencies contained in the detected ultrasonic wave. The transducer-based approach described in both of these prior art patents is unsuitable for use on processed metal surfaces, which tend to be relatively rough and uneven, and cannot be used for in-line monitoring during metal processing. In addition, the Rayleigh wave velocity measurements used by Lindgren are relatively insensitive to metal defects, and do not provide the directional information needed for detection of localized defects. Likewise, the ultrasonic frequency analysis used by Tittmann does not provide the directional information needed to locate subsurface defects.

In contrast, the present invention is based on detection and analysis of scattered Rayleigh waves to detect subsurface defects. The prior art provides no suggestion that scattered Rayleigh waves might be useful for defect detection. Another important aspect of the present invention is the use of laser generation and detection of Rayleigh waves so that the invention can be applied to relatively rough and uneven processed metal surfaces, and may be used for in-line monitoring during metal processing.

SUMMARY OF THE INVENTION

The present invention provides a laser-ultrasonic method and device that are useful for detection of defects within a processed region of a metallic workpiece. The method involves a pitch-catch approach whereby a surface acoustic wave (Rayleigh wave) is laser-generated at a first location on the workpiece surface, and a scattered portion of the generated Rayleigh wave is detected at a second location on the workpiece surface, along with the direct-arriving (unscattered) Rayleigh wave. The invention is particularly useful for detecting voids in laser cladded metallic layers and friction stir processed layers. The method of the invention may be used for in-line monitoring of laser cladding and friction stir processes, which generally result in a line or bead of processed metal having an appreciable width. The line of processed metal may be curved or straight.

In the method of the invention, a probe Rayleigh wave is generated in the workpiece by directing a generation laser beam of small dimensions to a predetermined generation area within the processed region of the workpiece. When the probe Rayleigh wave is scattered by a subsurface defect, the scattered Rayleigh wave is detected via the temporal displacement of the workpiece surface produced by the scattered Rayleigh wave. This surface displacement is measured using an interferometer and a detection laser beam of small diameter that impinges (interrogates) the workpiece at a detection spot within the processed region of the workpiece. A predetermined spatial relationship is maintained between the generation area and the detection spot. High sensitivity and resolution are attained via use of very small laser beam dimensions and a close spacing between the generation area and the detection laser spot. Sensitivity is typically highest when the detection laser spot overlaps at least a portion of the cross-sectional area of the defect when viewed along a line perpendicular to the surface of the metallic workpiece within the processed region. Further improvement in sensitivity may be provided via wavelet analysis of the detection signal.

In a preferred embodiment, the invention is used to detect defects in a line or bead of processed metal. In this case, the laser generation area preferably has the shape of a rectangle with the long sides of the rectangle substantially perpendicular to the line of processed metal. The laser generation area preferably spans the width of the line of the processed metal. In this case, the entire width of the processed metal line may be continuously monitored for defects in real time during the metal processing operation.

The method of the invention may also be used to provide an image of subsurface defects within the processed region of a metallic workpiece. In this case, measurements of acoustic waveforms (surface displacement magnitude vs. time) are made at regularly spaced locations along the processed workpiece surface, while a predetermined spatial relationship is maintained between the laser generation area and the detection laser spot. This may involve maintaining the generation and detection laser beams at stationary positions while the workpiece is moved so that the laser beams track along a line or bead of processed metal. Alternatively, the workpiece may be maintained in a stationary position while the laser beams are scanned along the surface of the processed metal. In either case, x-y raster scanning may also be employed. Preferably, the relative motion between the laser beams and the workpiece is such that both laser beams impinge the workpiece surface along the line of motion.

In one embodiment, a single waveform corresponding to a defect-free location is chosen as a reference, and the overall amplitude of each waveform is normalized to the amplitude of the reference waveform. A computer program is preferably used to calculate the Mean Square Error (MSE) between the reference waveform and each of the other waveforms in the raster scan. A plot of MSE intensity versus x-y location provides an image of defects in the processed metal.

In a preferred embodiment, the waveform acquired at each location on the workpiece surface within the processed metal region is analyzed using a wavelet transform. This analysis detects the characteristic changes in the waveform that are uniquely associated with scattering from subsurface defects.

The device of the present invention for detecting a defect in a processed metal comprises a generation laser, a detection laser, an interferometer and an analyzer, and may further comprise a translation stage.

The present invention provides significant advantages compared to prior art methods. A key advantage is that the laser-ultrasonic method and device of the invention can be used for in-line detection of metal processing defects, enabling 100% parts inspection and real-time process control. The invention may be applied to detection of defects in metals processed by a variety of methods, including laser cladding, laser welding, friction stir processing and friction stir welding. The invention permits each layer of a laser cladding process to be monitored for defects.

Further features and advantages of the invention will be apparent to those skilled in the art from the following detailed description, taken together with the accompanying drawings.

Figure 1:
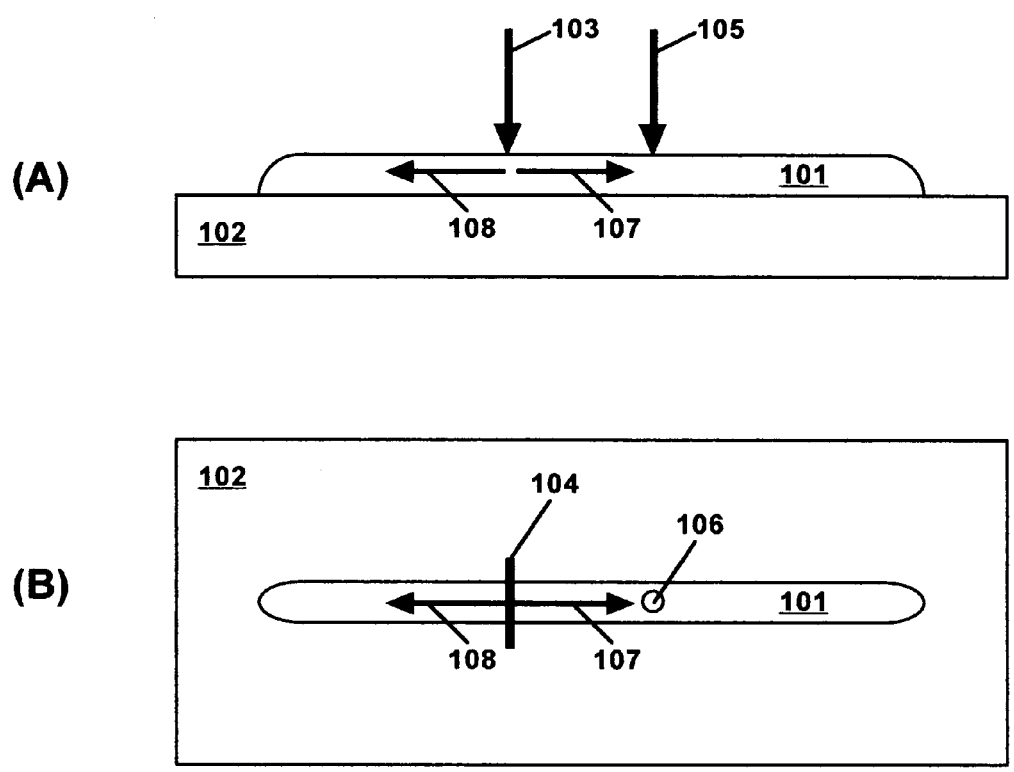
FIG. 1 depicts a side view (A) and a top view (B) schematically illustrating preferred shapes and locations for the laser generation area and the laser detection spot for detection of defects in a cladded bead on a workpiece.

These figures are not drawn to scale. Some features have been enlarged relative to other features for ease of depiction.

DETAILED DESCRIPTION OF THE INVENTION

Technical terms used in this document are generally known to those skilled in the art. The terms "subsurface" and "near-surface" are used interchangeably to denote defects residing near the workpiece surface at which the generation and detection laser beams are incident. The terms "Rayleigh wave", "surface acoustic wave" and "surface wave" are also used interchangeably. The term "workpiece" denotes any structure that includes processed metal, whether the metal processing is in progress or has been completed. The term "spot" is widely used in the art to denote a laser impingement area, which is typically circular and of small diameter. The terms used to denote the laser impingement areas of the present invention are "generation area" for the generation laser and "detection spot" for the detection laser. As used in this document, the terms "scattering" and "scattered" denote that a change in the direction of an ultrasonic wave propagated in a material occurs due to either deflection or reflection by a defect in the material.

The invention provides a laser ultrasonic method and device for detecting a subsurface defect within a processed region of a metallic workpiece. Subsurface defects that may be detected include voids, pores, bondlines, disbonds and cracks. The invention may be applied to detection of defects in metals processed by a variety of methods, including laser cladding, laser welding, friction stir processing, friction stir welding, and casting. It may also be applied to in-service inspection of railroad rails, and various other workpieces comprising processed metal. The invention is particularly advantageous for detecting defects in straight or curved lines of processed metallic material, but may also be applied to processed metal regions of other geometric shapes.

The device of the invention comprises: (1) a generation laser providing a generation laser beam that impinges a predetermined generation area on a surface of the metallic workpiece within the processed region; (2) a detection laser providing a detection laser beam that impinges (interrogates) the surface of the metallic workpiece at a detection spot which is within the processed region and has a predetermined spatial relationship to the generation area; (3) an interferometer that detects direct-arriving and scattered acoustic Rayleigh waves via the temporal displacement of the surface of the metallic workpiece at the detection spot based on the phase shift of a portion of the detection laser beam reflected from the surface of the metallic workpiece; and (4) an analyzer that compares the direct-arriving and scattered acoustic Rayleigh waves detected by the interferometer for at least two detection spots to detect the subsurface defect within the processed region of the metallic workpiece. The device of the invention may further comprise a translation stage for scanning to detect defects over a relatively large area of the workpiece, and optionally provide an image of the defect areas. The generation and detection lasers may be of any type that provides a suitable wavelength and sufficient power. A suitable generation laser is a Nd:YAG laser operating at a wavelength of 1064 nm and a pulse width of 10 ns (10-30 mJ per pulse). A suitable detection laser is a continuous wave frequency-doubled Nd:YAG laser operating at a wavelength of 532 nm (about one Watt of power).

FIG. 1 illustrates preferred shapes and locations of the generation area and the detection spot for detecting defects in a linear cladded bead 101 on a workpiece 102. Generation laser beam 103 impinges cladded bead 101 in generation area 104, which is preferably rectangular in shape with the long sides of the rectangle substantially perpendicular to the line defined by cladded bead 101. For a curved cladded bead (not shown), the long sides of the rectangular generation area would preferably be substantially perpendicular to the tangent to the curved line defined by the cladded bead. Preferably, the length of generation area 104 is substantially the same as the width of cladded bead 101, but may be larger (as shown) or smaller. If laser generation area 104 spans the width of cladded bead 101, the entire width of cladded bead 101 may be continuously monitored for defects in real time during the metal cladding operation. If laser generation area 104 is substantially longer than the width of cladded bead 101, a significant portion of the laser energy may be wasted. Detection laser beam 105 impinges cladded bead 101 in detection spot 106, which is located within cladded bead 101 and at a predetermined fixed distance from generation area 104. Typically, detection spot 106 is circular and has a diameter that is much smaller than the width of cladded bead 101.

During measurements according to the invention, the predetermined fixed distance between generation area 104 and detection spot 106 is maintained constant as workpiece 102 is moved relative to detection spot 106, or detection spot 106 is moved relative to workpiece 102, so that generation area 104 and detection spot 106 move along cladded bead 101. Typically, laser beams 103 and 105 are parallel and directed perpendicular to the surface of workpiece 102, and the relative motion is effected perpendicular to the laser beams so that the distance between the lasers and the surface of workpiece 102 remains constant. In one embodiment, the laser inspection system of the invention is stationary and the relative motion is provided by the machine used to perform the laser cladding operation. In another embodiment, the device of the invention further comprises a translation stage for scanning in one or two dimensions across the metallic workpiece surface relative to the fixed generation area and detection laser spot.

As also depicted in FIG. 1, generation laser beam 103 preferentially generates Rayleigh waves 107 and 108 that propagate perpendicular to the long sides of rectangular generation area 104, and travel in both directions along cladded bead 101. Forward Rayleigh wave 107, which travels in the same direction as generation area 104 and detection spot 106 relative to workpiece 102, arrives at detection spot 106 and is used to detect defects in cladded bead 101. Backward Rayleigh wave 107 does not arrive at detection spot 106 and is not used.

The method of the invention comprises the steps of: (1) generating a probe acoustic Rayleigh wave by directing a generation laser beam to a predetermined generation area on a surface of the metallic workpiece within the processed region; (2) detecting a direct-arriving and a scattered acoustic Rayleigh wave via an interferometer and a detection laser beam that impinges the surface of the metallic workpiece at a detection spot which is within the processed region and has a predetermined spatial relationship to the generation area; (3) repeating said step of generating and said step of detecting for a plurality of predetermined generation areas and detection spots on the surface of the metallic workpiece within the processed region; and (4) comparing the scattered acoustic Rayleigh wave detected for at least two predetermined detection spots to detect the subsurface defect within the processed region of the metallic workpiece. The step of comparing may include generating acoustic waveforms, directly comparing acoustic waveforms, calculating the Mean Square Error (MSE) between acoustic waveforms, generating B-scans, performing wavelet analysis, and combinations thereof. The scattered acoustic Rayleigh wave may be scattered substantially perpendicular to the direction of travel of the Rayleigh wave, or may be scattered at another angle.

Figure 2:
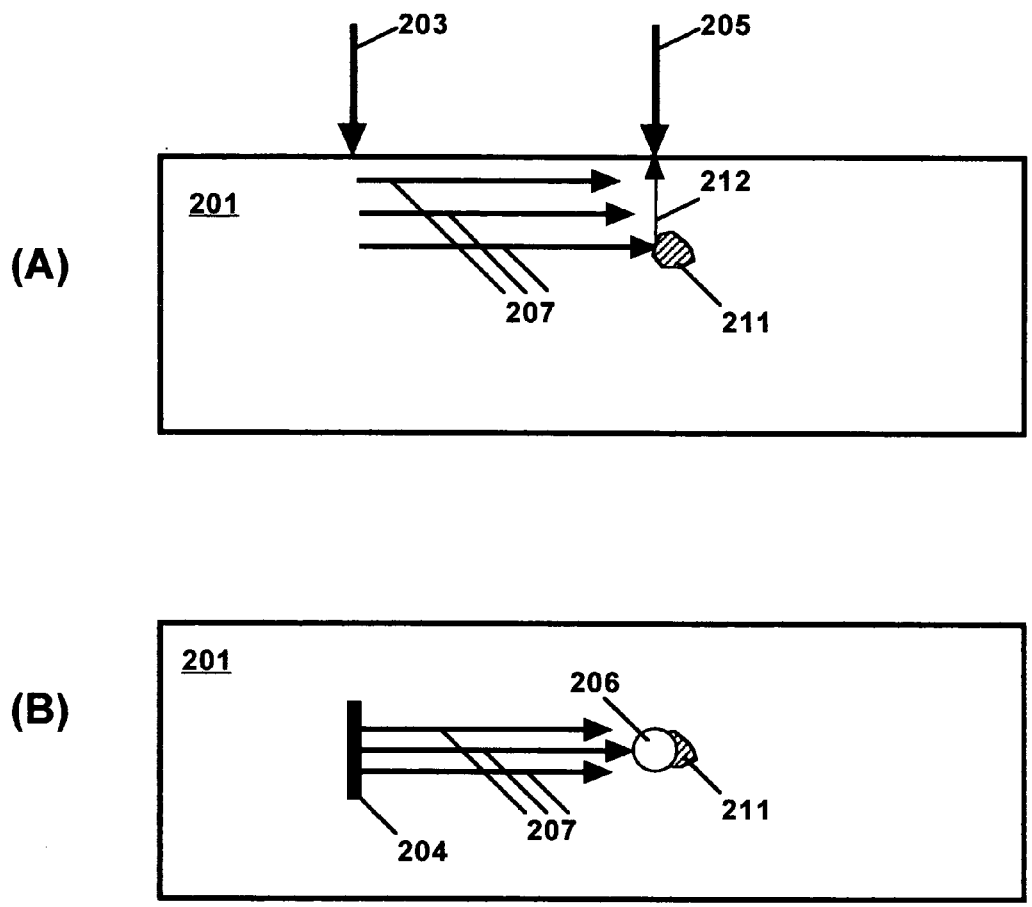
FIG. 2 depicts a side view (A) and a top view (B) schematically illustrating detection of a defect in a workpiece via Rayleigh waves scattered perpendicular to the direction of travel.

FIG. 2 illustrates a preferred embodiment by which a defect in a processed workpiece is detected via an acoustic wave derived from scattering of a Rayleigh wave perpendicular to its direction of travel. Rayleigh wave 207 is generated in workpiece 201 by generation laser beam 203 at generation area 204 and is scattered at defect 211 to generate acoustic wave 212. Scattered acoustic wave 212 may be detected at detection spot 206 via a reflected portion (not shown) of detection laser beam 205 and an interferometer (not shown). Note that Rayleigh waves (surface acoustic waves) are not confined strictly to the surface of the material of propagation but extend approximately one wavelength below the surface. This corresponds, for example, to a penetration depth in steel of about 3 mm for a Rayleigh wave of 1 MHz frequency. Consequently, subsurface defects at appreciable distances from the workpiece surface can be detected via scattering of surface acoustic waves (Rayleigh waves), according to the invention. Rayleigh wave 207 is represented by multiple (3) arrows in FIG. 2 to indicate its appreciable penetration depth.

The method of the invention generally provides highest sensitivity to defects when acoustic wave 212 is scattered at right angles to Rayleigh wave 207, and detection spot 206 at least partially overlaps defect 211 with respect to the perpendicular to the surface of workpiece 201 (as indicated in FIG. 1). In this case, the distance between detection spot 206 and defect 211 is minimized so that signal intensity loss due to dispersion of scattered acoustic wave 212 is minimized. Preferably, detection spot 206 is sufficiently small to enable resolution of defects that would significantly affect the properties of the processed metal of workpiece 201 with respect to its intended use. Larger spot sizes may be used, for example, to enable inspection of a larger workpiece area or processed metal line in a single inspection pass, or to minimize the number of inspection passes required.

The generation area width, the detection spot diameter, and the separation distance between these two laser impingement areas should be selected to provide temporal separation between the arrival times for the direct-arriving Rayleigh wave and the scattered acoustic wave that is sufficient for the measurement equipment to be used. For detection of defects in steel (Rayleigh wave velocity of approximately 3 mm/μs) with a detection bandwidth of 1-10 MHz (corresponding to a generation/detection pulse width of 100 ns), for example, requires that the width of the generation area and the diameter of the detection spot be 300 μm or less. Note that a generation laser pulse of 10 ns width generates Rayleigh waves having frequencies up to 100 MHz. Generally, the separation distance between the laser generation area and the laser detection spot should be as small as practical, preferably less than 4 mm center to center. For interrogation of relatively smooth surfaces using 300-μm laser beams, a separation distance of 3 mm is typically adequate. A typical spot size is approximately 100 μm, for which the beam separation distance can be reduced. Smaller separation distances (~1.5 mm) may be needed for interrogation of relatively rough surfaces, such as laser clad beads, for which the Rayleigh wave tends to be attenuated and distorted by scattering from random surface features. For separation distances less than ~1.5 mm, an ablation plasma produced by the generation laser may interfere with the detection process.

Figure 3:
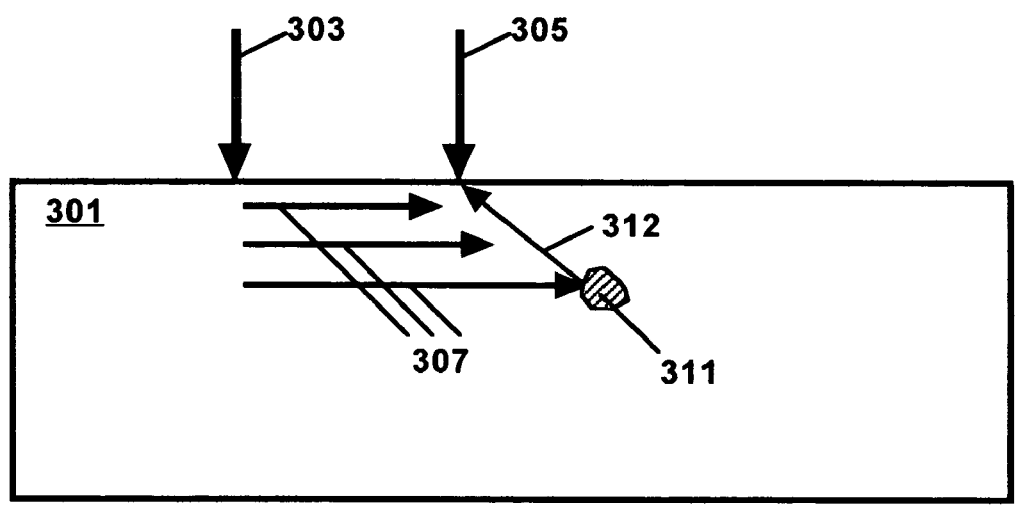
FIG. 3 depicts a side view schematically illustrating detection of a defect in a workpiece via backscattered Rayleigh waves.

Although a less preferred embodiment, subsurface defects in processed metals may also be detected according to the invention via Rayleigh waves scattered at angles other than 90° relative to the direction of travel. FIG. 3 illustrates detection of a subsurface defect in a workpiece via backscattered Rayleigh waves. In this case, Rayleigh wave 307 generated in workpiece 301 by generation laser beam 303 is reflected from defect 311 as backscattered acoustic wave 312, which is detected at the detection spot defined by detection laser beam 305. For this embodiment, detection sensitivity is reduced by dispersion of backreflected acoustic wave 312 over the greater distance between defect 311 and the detection spot (compared to that for scattering perpendicular to the Rayleigh wave). Scattered acoustic waves that impinge the workpiece surface at an angle greater than 90° also produce diminished surface displacement so that the measurement signal is further reduced. Likewise, forward scattered Rayleigh waves also provide reduced detection sensitivity.

Subsurface defects are detected according to the invention from the longer time required for the scattered acoustic wave, which must travel a greater distance compared to the direct-arriving Rayleigh wave, to arrive at the detection spot. Typically, the amplitude of the signal from a laser interferometer is plotted as a function of time (relative to the time at the end of the generation laser pulse) to produce an acoustic waveform. In the absence of scattering from defects, the acoustic waveform typically exhibits a single, relatively-sharp peak corresponding to the arrival time of the direct-arriving Rayleigh wave. Acoustic waves resulting from scattering at approximately 90° to the Rayleigh wave tend to broaden this peak toward longer times. Acoustic waves resulting from scattering at angles significantly greater than 90° to the Rayleigh wave tend to produce a shoulder or second peak of smaller amplitude at longer times (corresponding to a longer distance from the defect to the detection spot).

The method of the invention may be used to detect defects over relatively large areas of a processed metallic workpiece. In this case, acoustic waveforms are measured at regularly-spaced locations along the processed workpiece surface, while a predetermined spatial relationship is maintained between the laser generation area and the detection laser spot. This may involve maintaining the generation and detection laser beams at stationary positions while the workpiece is moved so that the laser beams track along a line or bead of processed metal. Alternatively, the workpiece may be maintained in a stationary position while the laser beams are scanned along the surface of the processed metal. In either case, x-y raster scanning may also be employed. Preferably, the relative motion between the laser beams and the workpiece is such that both laser beams impinge the workpiece surface along the line of motion.

The method of the invention may also be used to provide an image of subsurface defects within the processed region of a metallic workpiece. In one embodiment, a single acoustic waveform corresponding to a defect-free location is chosen as a reference, and the overall amplitude of each of the other acoustic waveforms is normalized to the amplitude of the reference waveform. A computer program is preferably used to calculate the Mean Square Error (MSE) between the reference waveform and each of the other waveforms in the raster scan. A plot of MSE intensity versus x-y location provides an image of defects in the processed metal.

An alternative approach for displaying an image of subsurface defects is the B-scan, which is false color or grey scale representation of the signal amplitude for acoustic waveforms measured at regular intervals in a substantially straight line along the workpiece surface. For the B-scan image, all of the acoustic waveforms are placed on the same time scale and the signal amplitude representation is displayed as a function of time (x-axis) and detection spot location (y-axis). In this case, the direct-arriving Rayleigh wave appears as a vertical line (or series of vertical lines), and defects are easily identified as a "bulge" along the time axis corresponding to the late-arriving scattered acoustic waves.

In a preferred embodiment, the waveform acquired at each location on the workpiece surface within the processed metal region is analyzed using a wavelet analysis. This analysis accents the characteristic changes in the waveform that are uniquely associated with scattering from subsurface defects so that the effects of extraneous signals, derived from workpiece surface roughness, for example, are minimized. Note that acoustic signals tend to be inherently nonstationary so that they are difficult to separate in the time domain or the Fourier frequency domain. Wavelet analysis, which involves an oscillating burst as the wavelet basis function, is well-suitable to laser-ultrasonic applications, for which the signal of interest is an oscillating burst. The discrete wavelet transform involved in wavelet analysis may be implemented via a bank of inexpensive finite impulse response (FIR) digital filters.

In wavelet analysis, the signal is treated as the weighted sum of overlapping wavelet functions. For a transient signal, most of the signal energy is assumed to be concentrated in relatively few of the wavelet coefficients, which contain most of the signal information. Wavelet analysis typically involves transforming the temporal signal into wavelet space, zeroing the coefficients that carry a large fraction of the original undistorted waveform and those that represent noise, and then transforming back into the time domain. This procedure effectively discards the part of the signal that contains no useful information about the defect. For the present invention, the transformed temporal signal resulting from wavelet analysis is much more sensitive to small changes resulting from defect scattering.

The invention may be used to detect subsurface defects within a processed region of a metallic workpiece while another area of the metallic workpiece is being processed, by laser cladding, for example. For laser cladded material built up of layers 1-2 mm thick, each layer may be inspected for defects before the next layer is deposited. Surface roughness may influence the measurement conditions and results but typically does not increase as layers are deposited since the surface of the previous layer is melted during deposition of the next layer.

DESCRIPTION OF A PREFERRED EMBODIMENT

The efficacy of the method of the invention was demonstrated by detecting simulated voids (blind holes) in stainless steel and titanium workpieces. Acoustic waveforms were generated using a pulsed Nd:YAG generation laser (1064 nm wavelength) that provided 10-ns pulses with an energy of 10-30 mJ per pulse (sufficient to produce mild ablation). Such pulses generate Rayleigh waves with frequencies up to 100 MHz. The generation area was rectangular with a width of 280 µm and a length of 3 mm. Detection was provided by a Lasson AIR-532-TWM laser ultrasonic receiver operating at a wavelength of 532 nm. This receiver has a bandwidth of 125 MHz and provided about one Watt of power to the detection spot, which was about 80 µm in diameter. The separation distance between the generation area and the detection spot was 3 mm (center to center).

EXAMPLE 1

Figure 4:
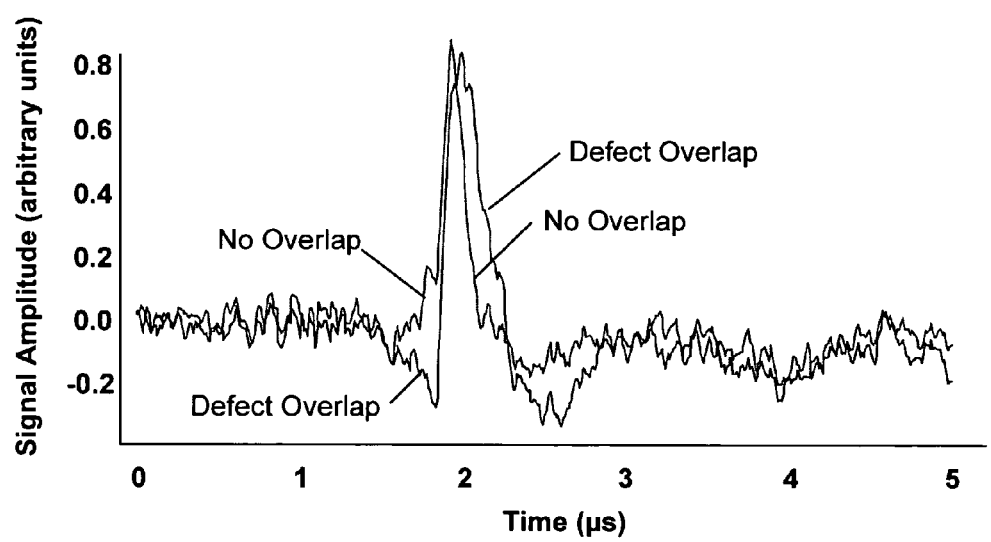
FIG. 4 shows acoustic waveforms obtained for a stainless steel plate without and with overlap of the detection spot with a simulated defect (blind hole 1.5 mm diameter and 0.4 mm deep).

FIG. 4 shows acoustic waveforms illustrating detection according to the invention of a simulated defect (blind hole 1.5 mm diameter and 0.4 mm deep in the back surface) in a machined stainless steel plate (6.4 mm thick). When the detection spot did not overlap the simulated defect, the acoustic waveform exhibited a relatively narrow peak (labeled "no overlap" in FIG. 4) corresponding to arrival of the direct-arriving Rayleigh wave, which was generated at a time of 1 µs in the plot of FIG. 4. When the detection spot did overlap the simulated defect, this peak (labeled "defect overlap" in FIG. 4) was broadened by the signal corresponding to arrival of the scattered acoustic wave at a later time.

EXAMPLE 2

A B-scan was generated for a machined stainless steel plate (6.4 mm thick) with a simulated defect (blind hole 1.5 mm diameter and 0.4 mm deep in the back surface). The defect was detected at the expected location in the B-scan as a time-delayed bulge in the vertical line corresponding to the direct-arriving Rayleigh wave.

EXAMPLE 3

A B-scan was generated for a machined titanium alloy 4-6 plate (6.7 mm thick) with a simulated defect (blind hole 1.0 mm diameter and 0.4 mm deep in the back surface). The defect was detected at the expected location in the B-scan as a time-delayed bulge in the vertical line corresponding to the direct-arriving Rayleigh wave. There is less grain scattering in titanium than in steel, so that more ultrasonic features were visible in the titanium plate. In addition to the bulge associated with direct scattering from the simulated defect, the B-scan exhibited two prominent diagonal lines that are associated with surface waves reflected from this defect. These diagonal lines, whose slopes depend on the surface wave velocity, may also be useful for defect detection and localization.

EXAMPLE 4

Figure 5:
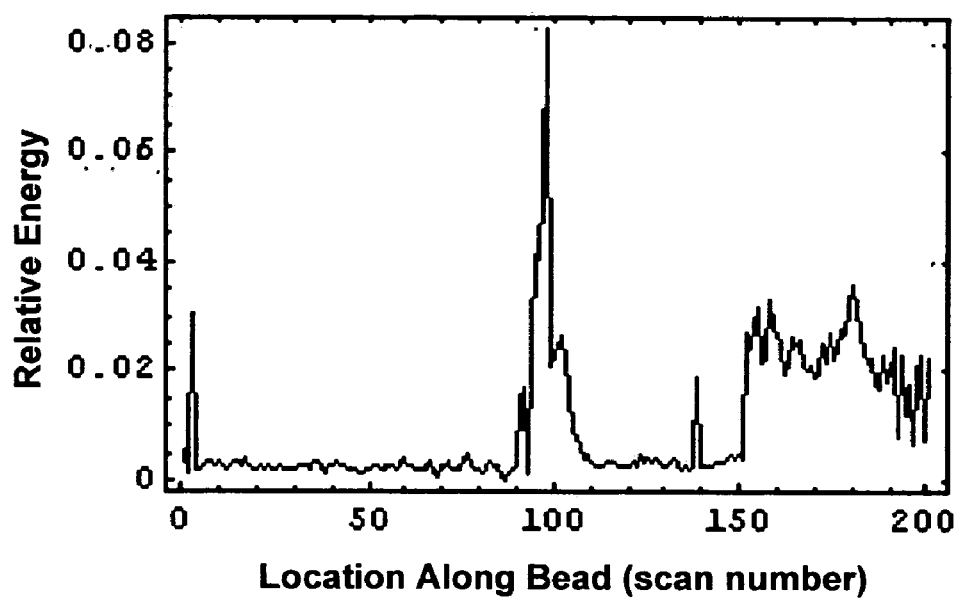
FIG. 5 shows a wavelet analysis plot of the relative energy at the fifth wavelet level for acoustic waveforms measured during a linear scan on a titanium alloy workpiece with a simulated defect (blind hole 1.0 mm diameter and 0.4 mm deep in the back surface).
Figure 6:
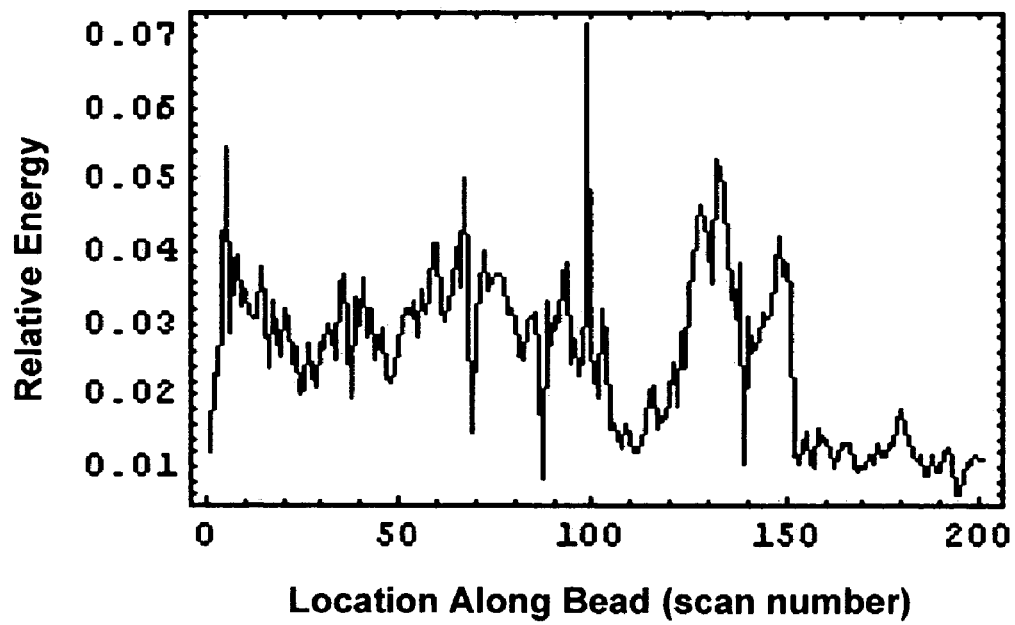
FIG. 6 shows a wavelet analysis plot of the relative energy at the sixth wavelet level for acoustic waveforms measured during a linear scan on the workpiece of FIG. 5.

The B-scan data for the titanium plate with the simulated defect (Example 3) was subjected to wavelet analysis. For each of 201 scans, the largest wavelet coefficients, which contributed 70% of the signal energy, were presumed to be associated with the unperturbed signal due to the direct-arriving Rayleigh wave and were zeroed out. Likewise, the smallest coefficients, which contributed 1% of the signal energy, were presumed to result from noise and were also zeroed out. Wavelet-processed temporal B-scans were constructed using the remaining (intermediate) coefficients, which were presumed to contain the information needed to provide improved defect contrast. FIGS. 5 and 6 show wavelet analysis plots of the relative energy at the fifth and sixth wavelet levels, respectively, for acoustic waveforms measured at various locations on the titanium alloy plate (Example 3). In both cases, a sharp peak is evident at scan 98, which is the expected location for the simulated defect.

The preferred embodiments of this invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A laser-ultrasonic method for detecting a subsurface defect within a processed region of a metallic workpiece, comprising the steps of:
    generating a probe acoustic Rayleigh wave by directing a generation laser beam to a predetermined generation area on a surface of the metallic workpiece within the processed region;
    detecting a direct-arriving and a scattered acoustic Rayleigh wave via an interferometer and a detection laser beam that impinges the surface of the metallic workpiece at a detection spot which is within the processed region and has a predetermined spatial relationship to the generation area;
    repeating said step of generating and said step of detecting for a plurality of predetermined generation areas and detection spots on the surface of the metallic workpiece within the processed region; and
    comparing the direct-arriving and scattered acoustic Rayleigh waves detected for at least two predetermined detection spots to detect the subsurface defect within the processed region of the metallic workpiece.

2. The method of claim 1, wherein the subsurface defect is a defect selected from the group consisting of void, pore, bondline, disbond and crack.

3. The method of claim 1, wherein the processed region is produced by laser cladding.

4. The method of claim 3, wherein the processed region is produced by friction stir processing.

5. The method of claim 1, wherein the processed region has the shape of a straight or curved line of processed metal.

6. The method of claim 5, wherein the generation area has the shape of a rectangle with the long sides of the rectangle substantially perpendicular to the line of processed metal.

7. The method of claim 6, wherein the generation area has a length that is substantially the same as the width of the line of processed metal.

8. The method of claim 1, wherein the detection spot overlaps at least a portion of the cross-sectional area of the defect when viewed along a line perpendicular to the surface of the metallic workpiece within the processed region.

9. The method of claim 1, wherein the generation laser beam has a wavelength of 1064 nm.

10. The method of claim 1, wherein the detection laser beam has a wavelength of 532 nm.

11. The method of claim 1, wherein the distance between the center of the generation area and the center of the detection spot is less than 4 mm.

12. The method of claim 1, wherein said step of comparing includes performing a wavelet analysis.

13. The method of claim 1, wherein the subsurface defect is detected within a processed region while another area of the metallic workpiece is being processed.

14. A laser-ultrasonic device for detecting a subsurface defect within a processed region of a metallic workpiece, comprising:
    a generation laser providing a generation laser beam that impinges a predetermined generation area on a surface of the metallic workpiece within the processed region;
    a detection laser providing a detection laser beam that impinges the surface of the metallic workpiece at a detection spot which is within the processed region and has a predetermined spatial relationship to the generation area;
    an interferometer that detects direct-arriving and scattered acoustic Rayleigh waves via the temporal displacement of the surface of the metallic workpiece at the detection spot based on a phase shift of a portion of the detection laser beam reflected from the surface of the metallic workpiece; and
    an analyzer that compares the direct-arriving and scattered acoustic Rayleigh waves detected by the interferometer for at least two detection spots to detect the subsurface defect within the processed region of the metallic workpiece.

15. The device of claim 14, further comprising a translation stage for scanning the metallic workpiece surface relative to the detection spot.

* * * * *